United States Patent [19]

Barany

[11] Patent Number: 5,117,009
[45] Date of Patent: May 26, 1992

[54] XANTHENYLAMIDE HANDLE FOR USE IN PEPTIDE SYNTHESIS

[75] Inventor: George Barany, Falcon Heights, Minn.

[73] Assignee: University of Minnesota, Minneapolis, Minn.

[21] Appl. No.: 576,232

[22] Filed: Aug. 31, 1990

[51] Int. Cl.$^5$ .......................................... C07D 311/88
[52] U.S. Cl. .................................. 549/394; 548/364; 548/358
[58] Field of Search ................. 549/394; 548/364, 358

[56] References Cited
FOREIGN PATENT DOCUMENTS

19697A/90  9/1991  Italy .

OTHER PUBLICATIONS

Caciagli, V. et al., *Proceeding of the European Peptide Symposium* (Sep. 1990), Abstract p. 97.
Albericio, F. et al., *J. Organ. Chem.* 55:3730-3743 (1990).
P. Sieber, *Tetrahedron Letters* 28:2107-2110 (1987).
Barany et al., *Int. J. Peptide Protein Res.* 30:703-739 (1987).

*Primary Examiner*—Nicky Chan
*Attorney, Agent, or Firm*—Hamilton, Brook, Smith & Reynolds

[57]  ABSTRACT

The preparation and properties of xanthenylamide handles for use in peptide synthesis is disclosed. The compounds, Fmoc-9H-2-alkyleneoxycarboxy-xanthene-9-amines, are used as peptide handles in the solid phase synthesis of peptide amides.

2 Claims, 3 Drawing Sheets

XANTHENYLAMIDE HANDLE FOR USE IN PEPTIDE SYNTHESIS

GOVERNMENT SUPPORT

This invention was made with government support under GM 42722 awarded by the National Institutes of Health. The government has certain rights in the invention.

BACKGROUND OF THE INVENTION

A number of naturally occurring peptides, including oxytocin, secretin, apamin, and several releasing hormones from the brain, are peptide amides, that is, they contain an amide function at the carboxyl terminal. The synthesis of C-terminal peptide amides is problematical because of the acid-sensitivity of these peptides, and the tendency of some amino acid residues, such as tryptophan, to become alkylated under the conditions used in most synthesis methods. The synthesis of peptide amides by solid-phase synthesis has most commonly involved releasing the peptide amide from the solid phase using either a strong acid (e.g., anhydrous hydrogen fluoride) or a strong base (e.g., ammonia) for final cleavage. For example, ammonolysis of benzyl and other ester anchoring linkages has been used, or benzhydrylamine support resins which are compatible with protection strategies that use anhydrous hydrogen fluoride (HF) for the final cleavage of the peptide from the support have been used. Such harsh conditions can cause undesirable side reactions. G. Barany and R. B. Merrifield, *In: The Peptides*, E. Gross and J. Meienhofer (eds.), Vol. 2, pp. 1-284, Academic Press, New York (1979).

Several drawbacks to these methods exist, for example, ammonolysis of sterically hindered amino acids, such as valine, proceeds very slowly, and is even further retarded with the increasing length of the peptide chain. In addition, this technique is limited to peptides lacking $C^\omega$-benzyl-protected aspartate or glutamate residues, which would be vulnerable to attack by ammonia. Finally, prolonged treatment with ammonia leads to partial racemization of Cys(Acm) residues.

Solutions which have been proposed for these problems include milder conditions and orthogonal protection schemes. An "orthogonal" system is defined as one using two or more independent classes of protecting groups which are removed by different chemical mechanisms. The most flexible approach for the solid phase synthesis of peptide amides appears to involve the use in orthogonal systems of handles which incorporate a precursor of the amide function. These handles are coupled onto amine-functionalized solid supports and serve as a starting point for peptide chain elongation. For example, handles which are useful for anchoring tert-butyloxycarbonyl (Boc)-protected amino acids to solid supports are described by Gaehde and Matsueda in *Int. J. Peptide Protein Res.*, 18: 451 (1981). Albericio and Barany describe handles for use with Fmoc-protected amino acids. F. Albericio and G. Barany, *Int. J. Peptide Protein Res.*, 30: 206-216 (1987); F. Albericio et al., *J. Organic Chemistry*, 55: 3730-3743 (1990). However, the synthesis and/or cleavage conditions used in the referenced methods are too harsh for some peptide amides. A handle which allows acid-sensitive peptide amides to be efficiently produced and cleaved from the support under mild conditions would be valuable.

SUMMARY OF THE INVENTION

The invention relates to novel compounds which can be used as handles for linking protected amino acids or peptides to a support during peptide synthesis. The compounds are Fmoc-xanthenylamide derivatives having the general formula:

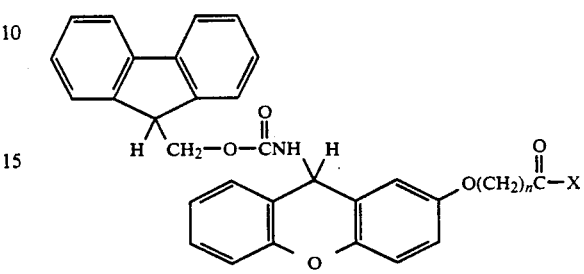

wherein n is an integer of from about 1 to about 10; and wherein X is OH or the activating group of an ester or thioester. X also represents the amide linkage to an amino-functionalized solid support. The compounds are used as handles for amino acids or peptides during solid phase peptide synthesis, in which they are linked to an amino-functionalized solid support or to an amino group of a spacer arm attached to a solid support. When the compounds are attached to the solid support, X represents the amino component of the amide linkage to the amino-functionalized support. The present compounds, which are omega-(9-(9-fluorenylmethyloxycarbonyl)aminoxanthen-2-oxy)alkanoic acid derivatives, are particularly useful for synthesizing peptides or proteins having amide groups in the C-terminal position ("peptide amides").

A method of preparing the present Fmoc-xanthenylamide compounds is also the subject of the present invention. The method involves alkylating hydroxyxanthone compounds with appropriate ω-halo acids or esters. The resulting intermediate is then reduced to yield the xanthydrol intermediate, which is then reacted with 9-fluorenylmethyl carbamate (Fmoc-NH$_2$) to yield the present xanthenylamide derivatives.

A method of synthesizing peptides or proteins utilizing the present compounds is also the subject of the present handle invention. In this method, the Fmoc group is removed and a first amino acid or peptide is attached to the xanthenyl portion of the handle, forming a C-terminal amide bond. The xanthenyl-linked amino acid or peptide is then attached to a solid resin or support, or to an amino group on a spacer arm attached to the solid support. The xanthenyl compound reacts through its side chain carboxyl group (represented by X) with the amino group, forming a stable amide linkage. This resin-linked amino acid or peptide amide serves as the starting point for chain elongation.

The present Fmoc-xanthenylamide compounds and method of using them in solid phase peptide synthesis have several advantages. Cleavage of the finished peptide or protein from the xanthenyl handle occurs under mild acid conditions, which allows direct preparation of acid sensitive conjugates. In particular, peptide amides which are sensitive to the acids used to cleave the finished peptide or protein from the handle can be efficiently produced using the present handles. Undesirable side reactions are minimized using the present compounds and method.

DETAILED DESCRIPTION OF THE INVENTION

The present Fmoc-xanthenylamide compounds have the following general formula:

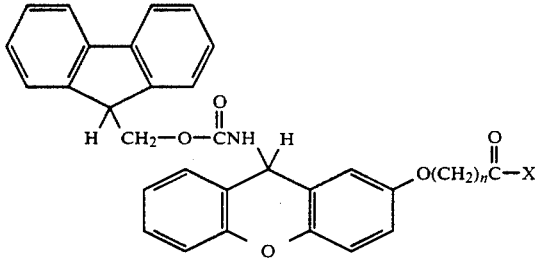

wherein n is an integer of from about 1 to about 10 and wherein X is OH, or the activating group of an ester or thioester. X also represents the amino component of an amide linkage when the compound is attached to an amino-functionalized solid support. The term "active ester" refers to compounds which activate the carboxyl groups of an amino acid or peptide. Active esters activate the carboxyl group by making it more reactive with an amino group on a support or on another amino acid or peptide. Activating groups which can be used in the present invention include, for example, trichlorophenyl (TCP) esters, pentafluorophenyl (PFP) esters, pentachlorophenyl (PCP) esters and methyl phenylpyrazolinone (Mpp) esters.

Figure 1:
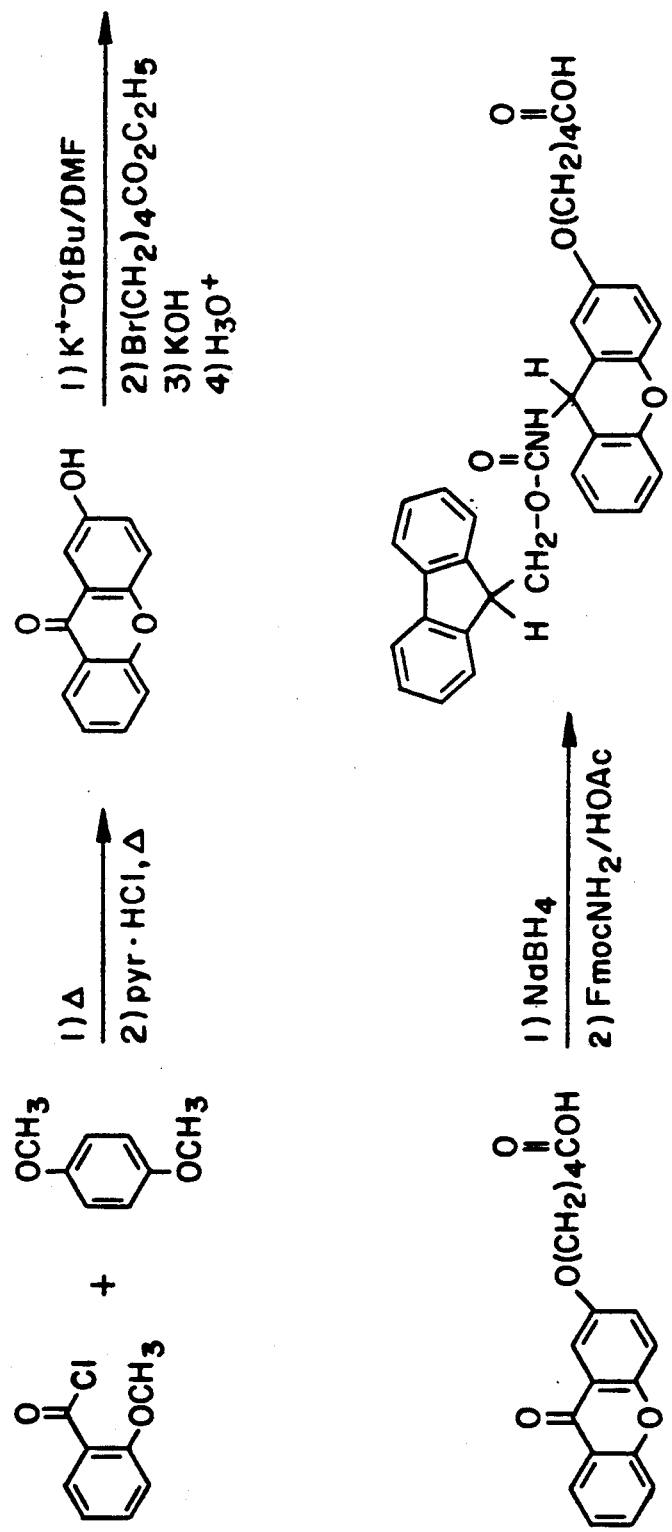
FIG. 1 is a schematic illustration of the synthesis of 5-(9-(9-fluorenylmethyloxycarbonyl)aminoxanthen-2-oxy)valeric acid.

The present xanthenyl compounds are generally known as omega-(9-(9-fluorenylmethyloxycarbonyl)aminoxanthen-2-oxy)alkanoic acid derivatives. The compounds are prepared from hydroxyxanthones which can be obtained as described in the literature precedents. R. A. Finnegan, et al., *J. Chem. Soc. Perkins Trans.*, 1: 1896 (1982); N. G. Steinberg, et al., *J. Heterocyc. Chem.*, 9: 1181 (1972); Z. M. Akhtar et al., *Org. Mass. Spectrom.*, 7: 667 (1973). The hydroxyxanthone compounds are alkylated with appropriate ω-halo acids or esters to introduce the eventual handle side-chain. The present method provides a successful route to generate a xanthydrol and trap it with Fmoc-amide, as illustrated in FIG. 1 for the 2-valeryl derivative (wherein n=4, and X is OH). The same chemistry can be carried out also for other derivatives, e.g., the 2-oxyacetyl derivative.

The xanthenyl handle is attached to aminofunctionalized supports or to the amine groups of spacer arms attached to solid supports. The present Fmoc-xanthenyl compounds react through their side chain carboxyl groups with amino groups, forming stable amide linkages. The reaction can be performed using standard coupling methods for creation of amide linkages, for example, N,N'-dicyclohexylcarbodiimide (DCC) or N,N'-diisopropylcarbodiimide (DIPCDI) plus 1-hydroxybenzotriazole (HOBt) coupling. See, F. Albericio et al., *J. Organic Chem.*, 55:3730-3743 (1990) the teachings of which are hereby incorporated herein by reference. The present compounds are attached by reacting about one equivalent of the present xanthenyl compounds for each equivalent of amino groups present on the support.

A variety of amino-functionalized supports can be used as the solid phase, for example, macromolecules or solids, such as membranes, porous glass, silica, polystyrenes, polydimethylacrylamides, cotton or paper. Functionalized polystyrene resins, such as amino-functionalized polystyrene, aminomethyl polystyrene, aminoacyl polystyrene, or p-methylbenzhydrylamine polystyrene resins can be used for this purpose. Polyethylene glycol-polystyrene (PEG-PS) graft co-polymers functionalized with amino groups are particularly useful solid phases. PEG-PS resins which can be used are described for example in co-pending U.S. application Ser. No. 07/576,634, entitled "Polyethylene Glycol Derivatives For Solid-Phase Applications" by Barany et al., filed concurrently herewith the teachings of which are incorporated herein by reference.

The resulting resin-linked handle is then reacted with a C-terminal amino acid or peptide which serves as the starting point for chain elongation. The amino acid or peptide is coupled to the handle according to the following procedure. The Fmoc group on the xanthenyl handle is first removed, for example, using piperidine-dichloromethane (1:1), and a protected amino acid or peptide is attached to the resulting amine group through its C-terminal carboxyl group by a standard method for creating amide linkages, such as DCC-mediated coupling. The resulting solid phase, having attached thereto the amino acid or peptide through the xanthenyl handle of the present invention, is ready for use in synthesizing a peptide or protein.

The first amino acid or peptide can also be coupled to the handle prior to attaching the handle to the solid support, using the coupling methods described above.

The resulting amino acid/peptide-handle-resin complex provides a well-defined starting structure for peptide chain elongation. Solid phase peptide synthesis can then be carried out by standard methods for synthesizing peptide amides. Solid phase synthesis typically begins with covalent attachment of the a-carboxyl end of an $N^\alpha$-protected amino acid to the amino acid or peptide linked to the handle. The synthesis cycle generally consists of deprotection of the α-amino group of the amino acid, washing, and, if necessary, a neutralization step, followed by reaction with a carboxyl-activated form of the next $N^\alpha$-protected amino acid. The cycle is repeated to form the peptide or protein of interest. Solid phase synthesis methods for peptide amides which can be used with the present xanthenyl handles include, for example, methods described by Albericio et al., *J. Org. Chem.*, 55:3730-3743 (1990); the teachings of which are hereby incorporated herein by reference.

Peptide synthesis using a solid support containing the present xanthenyl handles proceeds well, and final cleavage from the support is accomplished with a mild acid, such as dilute trifluoroacetic acid (TFA). TFA having a concentration of from about 3 to about 25% is useful in the present method, for example. The presence of at least four carbon atoms at the carboxyl end of the present derivatives is preferred. The presence of a four-carbon spacer in the valeryl derivative (where n=4), for example, leads to a 5-fold increase in acid lability over the corresponding analog having a one-carbon spacer (where n=1). It is even possible to release peptide amides made using the preferred xanthenyl compound (having a 4-carbon spacer, i.e., where n=4) with partial retention of side-chain tert-butyl protection.

In contradistinction to experiences with other handles, scavengers such as dimethyl sulfide, 1,2-ethanedithiol, anisole, thioanisole, and/or tri(isopropyl)silane are not required for high cleavage yields, nor for the optimal purity of tryptophan-containing peptides.

The handles of the present invention and methods of using them provide an efficient synthesis for peptide amides which are difficult to produce by other methods. For example, peptides containing tryptophan and/or tyrosine sulfate residues can be successfully made using the present compounds and methods. The method avoids the use of strong acids or bases and maximizes the yields and purities of the desired peptides which are obtained. In particular, the present handles provide excellent yields of tryptophan and tyrosine sulfate-containing peptide amides.

The invention will now be further illustrated by the following examples.

Exemplification

EXAMPLE 1

Preparation of 5-(9-(9-Fluorenylmethyloxycarbonyl)-aminoxanthen-2-oxy)acetic Acid 2,2',5-Trimethoxybenzophenone A mixture of o-anisoyl chloride (25.8 g, 0.15 mmol) and 1,4-dimethoxybenzene (37.2 g, 0.27 mol) was heated for 20 hours at 200° C., under $N_2$. Distillation led to recovered 1,4-dimethoxybenzene (18.7 g), b.p. 232° C. (8 mm) followed by the title product, shown below, (25.4 g, 63%), b.p. 232° C. (7 mm) which was suitable for carrying forward to the next step.

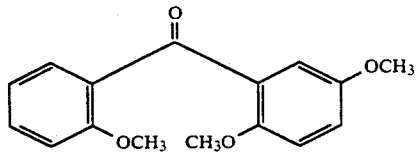

2-Hydroxyxanthone

A mixture of 2,2',5-trimethoxybenzophenone (6.52 g, 23,9 mmol, unpurified) prepared as described above, and pyridine hydrochloride (35.0 g, 0.3 mol) was refluxed (~210° C.) for 48 hours under $N_2$. The mixture was then poured into ice (100 g), and the yellow-green precipitate which formed was collected by filtration and washed with water (2×60 mL). This residue was then suspended in water (~60 mL), and made alkaline (pH~12) with 45% (w/v) aqueous KOH. The resultant reddish-brown suspension was filtered, and added dropwise to a stirred mixture of ice (50 g) and 12N HCl (15 mL). The precipitated solid was filtered, washed with water (4×20 mL), and air dried. Yield: 4.25 g (84%). TLC: $R_f$ 0.54 [benzene-EtOH (20:3)]. $^1$H-NMR (DMSO, 200 MHz) δ:8.17 (dd,J=1.5 and 7.9 Hz, 1H), 7.85 (t,J=7.7 Hz, 1H), 7.41–7.66 (m, 4H), 7.32 (dd,J=9.0 and 3.1 Hz, 1H).

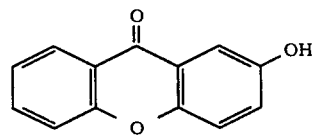

Ethyl(9-Oxoxanthen-2-oxy)acetate

A mixture of 2-hydroxyxanthone (4.39 g, 20.6 mmol) prepared as described above, ethyl bromoacetate (4.5 mL, 40 mmol), and anhydrous potassium carbonate (16.6 g, 0.12 mol) in acetone (200 mL) plus DMF (10 mL) was refluxed for 6 hours. The cooled reaction mixture was filtered to remove inorganic salts, washed with acetone (2×50 mL), concentrated, and placed under hexane whereupon crystals formed. Yield: 4.87 g (79%), TLC: $R_f$ 0.81 [one spot, benzene-EtOH (20:3)], m.p. 122°–123° C.; $^1$H-NMR (CDCl$_3$, 200 MHz) 8.32 (d,J=7.9 Hz, 1H), 7.63–7.75 (m, 2H), 7.33–7.50 (m, 4H), 4.74 [s, 2H, OCH$_2$(C=O)], 4.29 (q,J=7.1 Hz, 2H), 1.32 (t,J=7.1 Hz, 3H).

Anal. Calcd. for $C_{17}H_{14}O_5$, m.w. 298.28: C, 68.45; H, 4.73. Found: C, 68.65; H, 5.01.

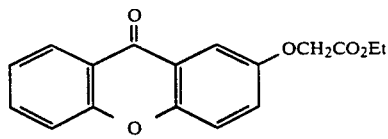

(9-Oxoxanthen-2-oxy)acetic Acid, Potassium Salt and Free Acid

Ethyl (9-oxoxanthen-2-oxy)acetate (3.33 g, 11.1 mmol) prepared as described above, was dissolved in 95% EtOH (50 mL), and 4N aqueous KOH (10 mL) and water (5 mL) were added. The mixture was stirred for 35 minutes at 35°–40° C. and then cooled. The solid precipitate was filtered, washed with absolute ether (3×10 mL), and air-dried. The structure of the potassium salt is shown below. Yield: 2.98 g (93%). TLC, $R_f$ 0.90 [MeOH-H$_2$O(4:1)]; $^1$H-NMR (D$_2$O) δ:6.9–7.8 (m, 7H), 4.14 (s, 2H).

The potassium salt formed as above was used directly in the next reaction. However, for further characterization, it was converted to the free acid (to pH~1) with 12N HCl. The free acid had a melting point of 179°–182° C.

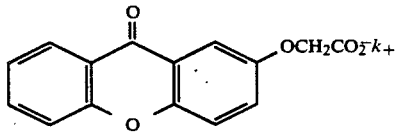

(9-Hydroxyxanthen-2-oxy)acetate, Mixture Sodium/Potassium Salts

A solution of potassium (9-oxoxanthen-2-oxy)acetate (8.48 g, 27.5 mmol) prepared as described above, in water (70 mL) was treated with NaBH$_4$ (2.0 g, 52.8 mmol) which was added in small portions over 1.5 hours while stirring. After 20 hours at 25° C., further NaBH$_4$ (1.0 g, 26.4 mmol) was added, and reduction was continued for 26 hours at 25° C. The resultant white precipitate was filtered, washed with EtOH (3×50 mL), combined with a second crop which appeared after partial concentration of the mother liquor, and air-dried. Yield: 7.2 g (89%); TLC $R_f$=0.22, [EtOH-H$_2$O-EtOAc (12:1:1); major spot which became yellow after spraying with 2% CF$_3$COOH in CH$_2$Cl$_2$]. $^1$H NMR (DMSO, 200 MHz) δ7.52 (d,J=8.0 Hz) 7.35–7.0 (m, 4H), 6.74 (dd,J=3.0 and 8.0 Hz, 1 Hz), 5.61 (s, 1H), 4.12 (s, 2H).

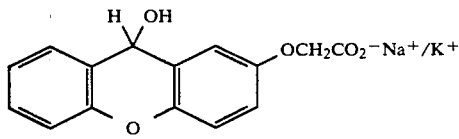

5-(9-(9-Fluorenylmethyloxycarbonyl)aminoxanthen-2-oxy)acetic Acid

A solution of Fmoc-amide (0.91 g, 3.64 mmol) in glacial acetic acid (30 mL) was added to a solution of (9-hydroxyxanthen-2-oxy)acetate salt mixture (1.0 g, 3.34 mmol) prepared as described above in acetic acid (55 mL). Next a solution of p-toluenesulfonic acid (0.1 g, 0.5 mmol) in acetic acid (10 mL) was added over 20 minutes, and the reaction mixture was stirred for 24 hours. The product slowly precipitated as a white solid, which was filtered, washed with water (4×10 mL), and dried in vacuo over P$_2$O$_5$. Yield: 1.34 g (83%). TLC pure, $R_f$: 0.54 (Me$_2$CO/EtOH/H$_2$O 12:1:1) orange color after spraying with 2% CF$_3$COOH/CH$_2$Cl$_2$. $^1$H NMR (DMSO 200 MHz) δ8.35 (d, NH), 6.9–7.7 (m, 15H), 5.69 (d, 1H) 4,63 (s, 2H), 4.37 (d, 2H) 4.23 (t, 1H).

Anal. Calcd. for C$_{30}$H$_{23}$NO$_5$.H$_2$O, MW:495.50: C, 72.71; H, 5.08; N, 2.82. Found: C, 73.06; H, 4.95; N, 3.01 (C, 73.16; H, 4.91; N, 3.06).

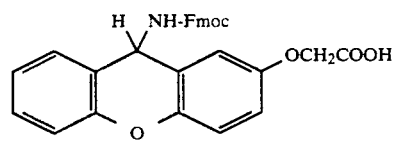

EXAMPLE 2

Preparation of 5-(9-(9-Fluorenylmethyloxycarbonyl)aminoxanthen-2-oxy)valeric Acid Ethyl 5-(9-oxoxanthen-2-oxy)valerate 2-hydroxyxanthone (7.7 g, 36 mmol) prepared as described in Example 1, was dissolved in DMF (50 mL), and potassium tert-butoxide (4.6 g, 41 mmol) was added in one portion. The mixture was stirred under N$_2$ at 25° C. for 1.5 hours, and then ethyl 5-bromovalerate (8.74 g, 42 mmol) in DMF (20 mL) was added dropwise over 20 minutes. The reaction mixture was heated at 115° C. for 11 hours, then cooled, filtered, and washed with EtOAc (2×10 mL). The filtrate was concentrated to provide a light-brown oily residue, which slowly solidified at room temperature. Light-beige crystals were collected and washed with n-hexane (3×10 mL). TLC pure, $R_f$=0.79 benzene-EtOH 10:9. Yield: 9.70 g (79%). A small amount of the product was recrystallized from n-hexane-EtOH (10:1) for elemental analysis. White needles, $^1$H-NMR (CDCl$_3$δ: 8.34 (dd, J=1.6 and 8.0 Hz, 1H), 7.66–7.76 (m, 2H), 7.3–7.5 (m, 4H), 4.14 (q, J=7.1 Hz, 2H), 2.40 [t,J=6.9 Hz, 2H, CH$_2$(C=O)] 1.85 (m, 4H), 1.26 (t,J=7.1 Hz, 3H-CH$_3$).

Anal. Calcd. C$_{20}$H$_{20}$O$_5$, MW: 340.36 Calculated: C, 70.57; H, 5.92. Found: C, 70.52; H, 5.86.

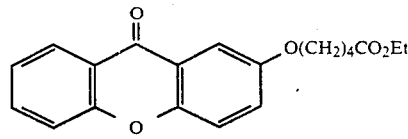

5-(9-Oxoxanthen-2-oxy)valeric Acid

Ethyl 5-(9-oxoxanthen-2-oxy)valerate (8.0 g, 24 mmol) prepared as described above was dissolved in a mixture of benzene (10 mL), 95% EtOH (40 mL), and water (5 mL), and 4N aqueous KOH (8 mL) was added. The mixture was refluxed for 6 hours (reaction complete by TLC), and partially concentrated (final volume ~10 mL). Absolute EtOH (10 mL) was added, and the resulting white precipitate was collected and washed with EtOH (2×10 mL). Yield: 1.7 g (21%), of potassium salt. The filtrate was evaporated, and the residue was dissolved in water (100 mL). The aqueous solution was extracted with EtOAc (3×20 mL), and the aqueous phase was added dropwise to a mixture of ice-water (100 mL) and 12N aqueous HCl (15 mL). A light-gray precipitate formed, which was collected, washed with water (3×10 mL), and dried. Yield: 5.45 g (74%) of free acid. A small amount of the product was recrystallized from n-hexane-EtOH (10:1) for elemental analysis. Fine white needles.

Anal. Calcd. C$_{18}$H$_{16}$O$_5$ (free acid), MW:312.31 Calculated: C, 69.21; H, 5.16. Found: C, 69.15; H, 5.01.

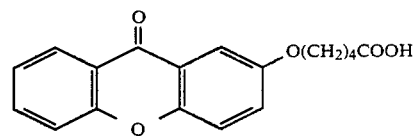

5-(9-Hydroxyxanthen-2-oxy)valeric Acid 5-(9-oxoxanthen-2-oxy)valeric (0.5 g, 1.6 mmol) prepared as described above was dissolved in water (20 mL), and 1N aqueous NaOH (2 mL) was added, followed by NaBH$_4$ (0.5 g, 13.2 mmol), in small portions over 1 hour. The mixture was stirred at 25° C. for 3 hours (TLC showed no starting ketone), and then acetone (20 mL) was added to decompose excess borohydride. The mixture was partially concentrated in vacuo at 25° C., and the remaining aqueous solution added dropwise to a well-stirred mixture of ice-water (20 mL) and glacial acetic acid (10 mL). The immediate precipitate was collected, washed with water (3×10 mL) and air-dried. Yield: 0.42 g (84%). There was a very small amount of by-product ($R_f$=0.02) in TLC; the main product $R_f$=0.51; [EtOAc-MeOH(4:2); major spot which became yellow after spraying with 2% CF$_3$COOH in CH$_2$Cl$_2$]. $^1$H NMR (d$_6$-acetone) δ:6.6–7.2 (m, 7H), 5.65 (s, 1H), 4.03 (s, 2H), 2.85 (s, 2H), 2.37 (s, 2H), 1.80 (s, 2H).

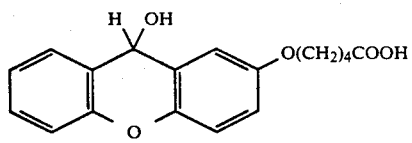

5-(9-(9-Fluorenylmethyloxycarbonyl)aminoxanthen-2-oxy)valeric Acid

A solution of p-toluenesulfonic acid (30 mg, 0.015 mmol) in glacial acetic acid (3 mL) was added dropwise at 25° C. over 15 minutes to a solution of 5-(9-hydroxyxanthen-2-oxy)valeric acid (0.2 g, 0.64 mmol) prepared as described above and Fmoc-NH$_2$ (184 mg, 0.76 mmol) in glacial acetic acid (12 mL). This mixture was stirred continuously for 14 hours, filtered, and the resultant white solid washed with water (3×5 mL) and n-hexane (2×5 mL). The solid was dried in vacuo over P$_2$O$_5$ at 25° C. for 6 hours. Yield: 200 mg (69%), TLC-pure R$_f$: 0.53 EtOAc/MeOH 10:2. $^1$H-NMR (CDCl$_3$, 300 MHz) δ7.76 (d, 7.4 Hz 2H), 7.59 (d, 7.4, 2H), 7.40 (t,J=7.4, 2H), 7.31 (t,J=7.4 2H), 4.69 (s, broad, 1H), 4.40 (d, J=6.9, 2H), 4.24 (t,J=6.9, 1H).

Anal. Calcd. C$_{33}$H$_{29}$NO$_5$, MW: 535.57 Calculated: C, 74.00; H, 5.45; N, 2.61. Found: C, 73.85; H, 5.46; N, 2.45.

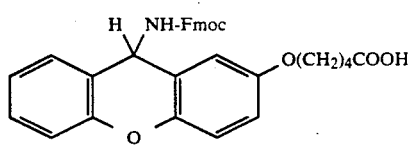

EXAMPLE 3

Preparation of Tabanus Peptide

An octapeptide derived from *Tabanus atratus*, the tabanus adipokinetic hormone peptide, was synthesized using the 5-(9-(9-fluorenylmethyloxycarbonyl)aminoxanthen-2-oxy)valeric acid (Fmoc-XAL) handle attached to a PEG-PS solid support. This octapeptide, which has the sequence:

pGlu-Leu-Thr-Phe-Thr-Pro-Gly-Trp-NH$_2$ is difficult to synthesize by most solid phase synthesis methods due to the presence of the tryptophan amide moiety, which is prone to alkylation.

In the present procedure, Fmoc-XAL was produced as described in Example 2. The Fmoc-XAL handle was coupled to Nle PEG-PS resin (loading: 0.1 mmol/g) using the DIPCDI/HOBt coupling procedure, as described by F. Albericio et al., in *J. Org. Chem.*, 55:3730-3743 (1990). The synthesis of the octapeptide was carried out using Milligen/Biosearch 9050 continuous flow synthesizer (Milligen/Biosearch, Novato, Calif.). The procedure was performed using the "standard Fmoc protocol" according to the manufacturer's instructions, using 10 equiv. each of Fmoc-amino acid and DIPCDI. At the end of each synthesis, cleavage of the peptide from the resin was performed according to the following procedure. The resin-bound peptide was suspended in a cocktail containing 5% trifluoroacetic acid (TFA), 10% scavengers (thioanisole and anisole) and 85% dichloromethane (CH$_2$Cl$_2$) for 1 hour. The mixture was filtered to remove the resin and the filtrate was collected. A second cocktail was added to the filtrate, containing 85% TFA, 5% CH$_2$Cl$_2$ and 10% of the scavengers. After 1 hour of reaction to remove tert-butyl groups, two volumes of acetic acid/water (3:7) was added to the mixture, resulting in separation into two phases. The organic (CH$_2$Cl$_2$) phase was removed, and the aqueous (acetic acid) phase was extracted once with CH$_2$Cl$_2$ and lyophilized.

Figure 2:
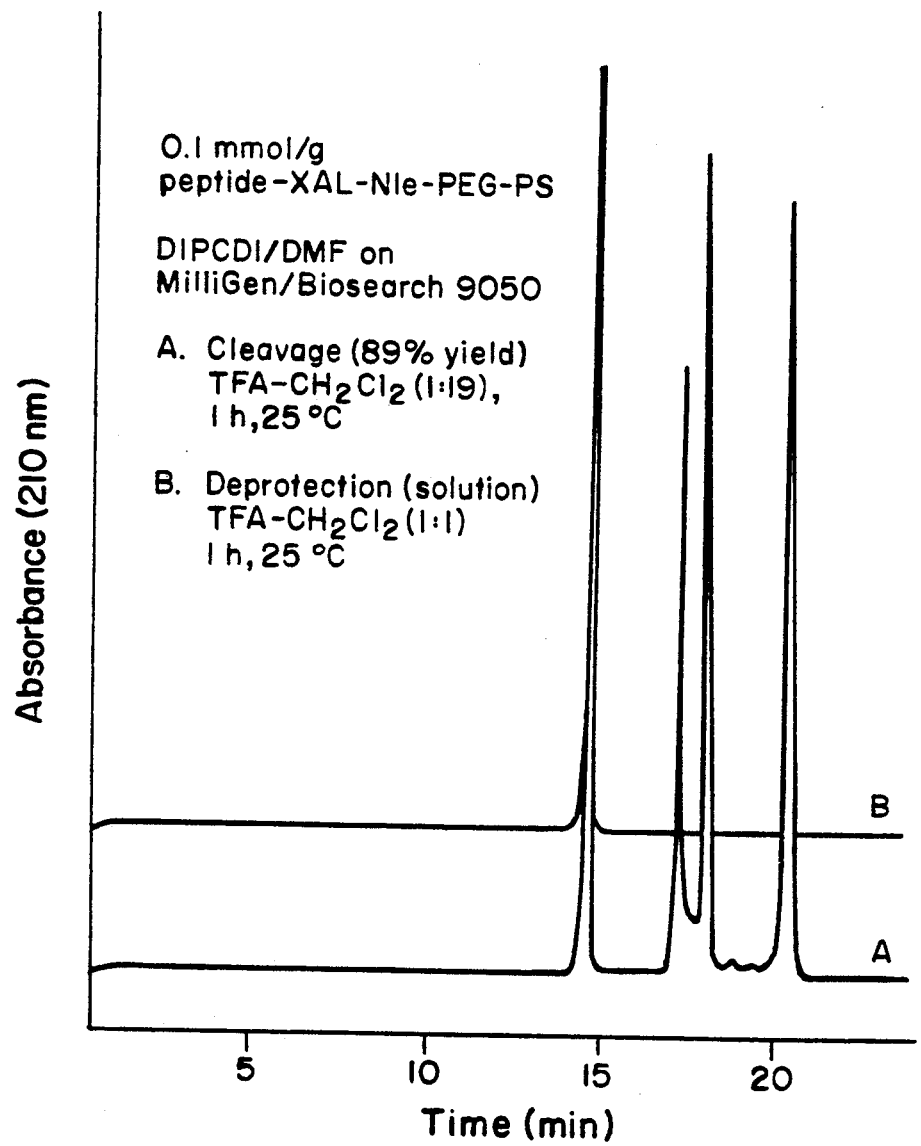
FIG. 2 is an HPLC chromatogram illustrating the results obtained synthesizing Tabanus Adipokinetic Hormone using the XAL handle.

The peptide obtained by this process was analyzed by high performance liquid chromatography (HPLC). The results are shown in FIG. 2. The yield of the octapeptide was about 90%. Amino Acid Analysis (AAA) was performed, and the results showed the following composition: Thr 1.77, Glu 1.05, Pro 0.96, Gly 1.01, Leu 0.99, Phe 0.98, which is characteristic of the tabanus peptide. The excellent cleavage yield indicates that negligible Trp alkylation took place.

EXAMPLE 4

Preparation of CCK-8 Peptide

The CCK-8 peptide was synthesized as described in Example 4 using the same handle. CCK-8 peptide is difficult to synthesize because it contains two methionine and one tryptophan residues. CCK-8 peptide has the amino acid sequence:

H-Asp-Tyr-Met-Gly-Trp-Met-Asp-Phe-NH$_2$

The yield of CCK-8 peptide was about 95%. AAA showed a composition of: Asp 2.03, Gly 1.04, Met 1.92, Tyr 0.99, Phe 1.02, which is characteristic of CCK-8.

EXAMPLE 5

Preparation of CCK-8 Sulfate Peptide

Figure 3:
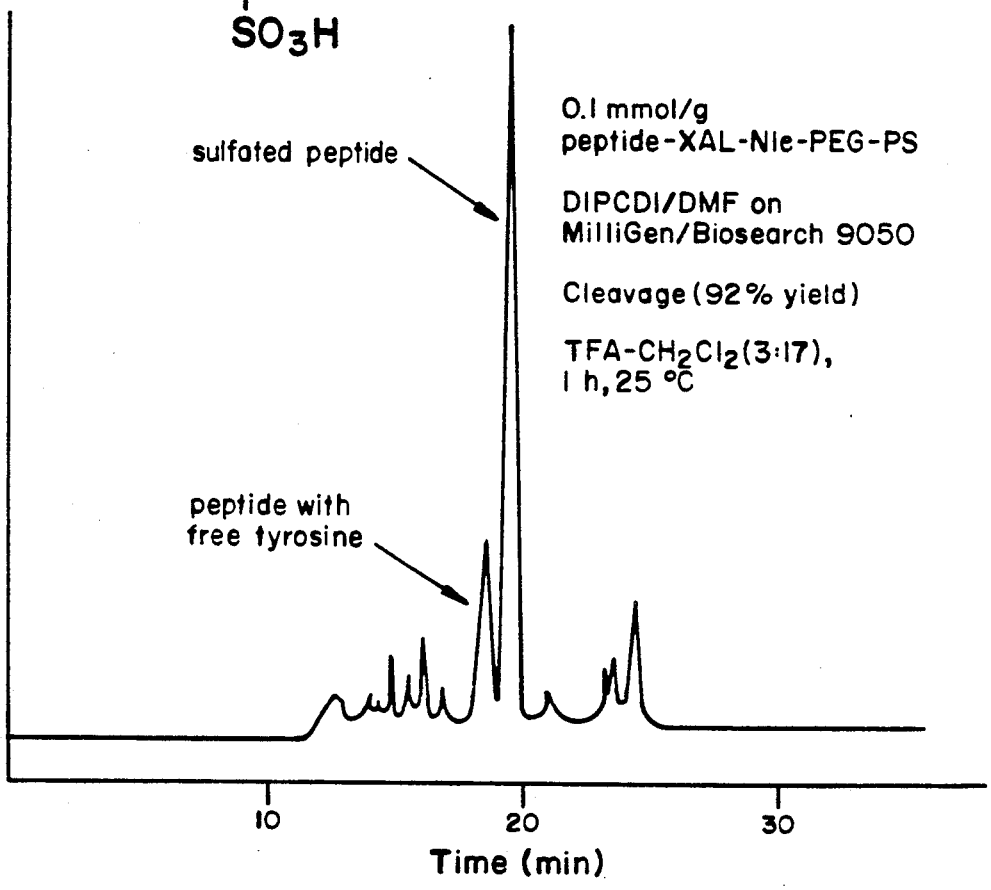
FIG. 3 is an HPLC chromatogram illustrating the results obtained in synthesizing CCK-8 sulfate using the XAL handle.

The CCK-8 sulfate peptide was synthesized according to the procedure described in Example 3. CCK-8 sulfate is very difficult to synthesize because it contains tyrosine sulfate, which is labile to acid. CCK-8 peptide has the same sequence as CCK-8 peptide except that it contains a tyr-sulfate residue in place of the tyr residue of CCK-8. The procedure was the same as set out in Example 4 for CCK-8 except that 15% TFA in CH$_2$Cl$_2$ without the scavengers was used. The HPLC results are shown in FIG. 3. The yield of CCK-8 sulfate peptide was about 92% and AAA showed the following composition:

Asp 2.05, Gly 1.02, Met 1.82, Tyr 0.97, Phe 0.96.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A xanthenylamide compound for use in peptide synthesis having the formula:

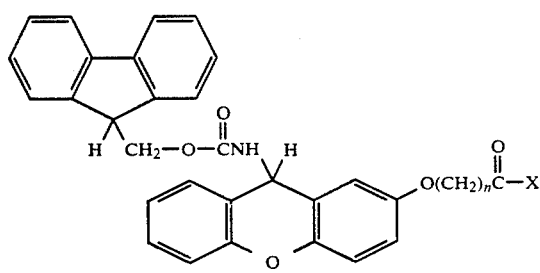
wherein n is an integer from about 1 to about 10; and X is hydroxyl or the activating group of an active ester or thioester.
2. A compound of claim 1, wherein n is 4 and X is OH.
* * * * *